US00RE42755E

(19) United States
(12) Reissued Patent
Molan

(10) Patent Number: US RE42,755 E
(45) Date of Reissued Patent: Sep. 27, 2011

(54) HONEY BASED WOUND DRESSING

(75) Inventor: Peter Molan, Hamilton (NZ)

(73) Assignee: Apimed Medical Honey Limited, Cambridge (NZ)

(21) Appl. No.: 12/420,344

(22) PCT Filed: Dec. 11, 2000

(86) PCT No.: PCT/NZ00/00248

§ 371 (c)(1), (2), (4) Date: Nov. 12, 2002

(87) PCT Pub. No.: WO01/41776

PCT Pub. Date: Jun. 14, 2001

Related U.S. Patent Documents

Reissue of:
(64) Patent No.: 6,956,144
Issued: Oct. 18, 2005
Appl. No.: 10/149,116
Filed: Nov. 12, 2002

(30) Foreign Application Priority Data

Dec. 9, 1999 (NZ) ..... 501687
Dec. 13, 1999 (NZ) ..... 501748

(51) Int. Cl.
*A61F 13/00* (2006.01)
*A61K 31/74* (2006.01)
*A61L 15/16* (2006.01)

(52) U.S. Cl. ..... 602/48; 424/78.06; 424/447; 604/304

(58) Field of Classification Search ..... 602/48, 602/41–43; 604/304–308; 424/443–449, 424/78.06, 70.11; 128/888, 889
See application file for complete search history.

(56) References Cited

U.S. PATENT DOCUMENTS 5,482,932 A 1/1996 Thompson
5,785,972 A * 7/1998 Tyler ..... 424/764
5,980,875 A * 11/1999 Mousa ..... 424/70.11
2004/0127826 A1* 7/2004 Caskey ..... 602/41

FOREIGN PATENT DOCUMENTS

CH 653892 A5 * 1/1986
EP 0258761 B1 3/1988
EP 0 355 356 2/1990

(Continued)

OTHER PUBLICATIONS

Wood et al., Manuka Honey, a low cost leg ulcer dressing, the New Zealand Medical Journal, vol. 110, Issue 1040, Mar. 1997, p. 107.*

(Continued)

*Primary Examiner* — Kim M Lewis
(74) *Attorney, Agent, or Firm* — Sughrue Mion, PLLC

(57) ABSTRACT

The present invention is directed to the use of honey in medical dressings. Preferred embodiments modify honey with a viscosity increasing agent, resulting in a range of possible compositions including ointments and salves, self-adhesive gels such as for use on mouth ulcers and pustules, and pliable or flexible sheets which can be used as a wound covering. Preferred viscosity increasing agents include both particulate and continuous gels, respective examples of each including agars and alginates. Selected honeys preferably, but not necessarily, exhibit antibacterial properties other than what is merely conferred by osmolarity and sugar concentration effects.

52 Claims, 1 Drawing Sheet

FOREIGN PATENT DOCUMENTS

| | | | | |
|---|---|---|---|---|
| EP | 0355536 | | * | 2/1990 |
| EP | 0460588 | | * | 12/1991 |
| EP | 04 89206 | A1 | * | 6/1992 |
| EP | 0532275 | A1 | | 3/1993 |
| EP | 0 909 557 | | * | 4/1999 |
| GB | 2382527 | A | * | 6/2003 |
| WO | WO9736501 | | * | 10/1997 |
| WO | 199909933 | A1 | | 3/1999 |
| WO | WO9955349 | | * | 11/1999 |

OTHER PUBLICATIONS

Molan,P.C., et al., "The effects of gamma-irradiation on the antibacerial activity of honey", Journal of Pharmacy and Pharmacology, vol. 48, No. 11, 1996, pp. 1206-1209.*

Allen K.L., et al., "A Survey of the Antibacterial Activity of Some New Zealoand Honeys", Journal of Pharmacy and Pharmacology, vol. 43, No. 12, 1991, pp. 817-822.*

* cited by examiner

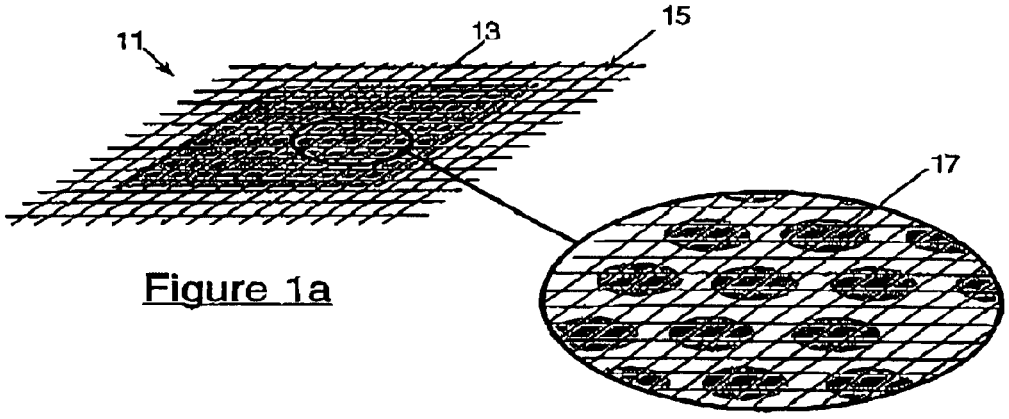
Figure 1a
Figure 1b
Figure 2
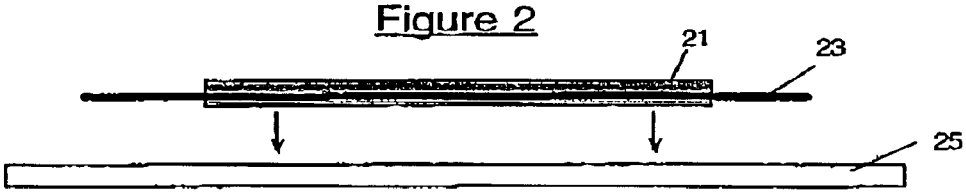
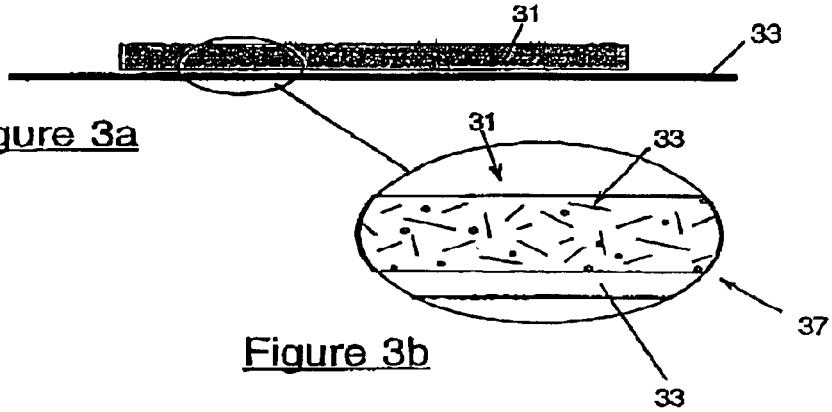
Figure 3a
Figure 3b

HONEY BASED WOUND DRESSING

Matter enclosed in heavy brackets [ ] appears in the original patent but forms no part of this reissue specification; matter printed in italics indicates the additions made by reissue.

TECHNICAL FIELD

The present invention is directed to the use of honey in medical dressings Preferred embodiments modify honey with a viscosity increasing agent resulting in a range of possible compositions including ointments and salves, self-adhesive gels such as for use on mouth ulcers and pustules, and pliable or flexible sheets which can be used as a wound covering.

Alternatively the invention may be viewed as an improvement on prior art "moist wound dressings" by incorporating honey in the gel to potentially confer to such dressings anti-bacterial properties, anti-inflammatory properties, debriding qualities, and promotion of growth of wound tissue

BACKGROUND ART

The use of honey in treating wounds have been long known, with such use being recorded in 4,000 year old Sumerian clay tablets. There are continuing records of its use throughout history, with an increasing number of medical reports near the beginning of this century. Recently the anti-bacterial properties of honey and its potential use as a wound dressing has attracted greater attention.

Recent international medical literature record honey as being effective as a dressing for wounds, burns and skin ulcers. Recorded observations include that inflammation, swelling and pain are quickly reduced, that sloughing of necrotic tissue occurs without the need for debridement, and that growth of tissues to repair the wound is stimulated. As a consequence, healing occurs rapidly with minimal scarring, and often without any necessity for skin rafting.

Work by the inventor and others has helped to establish that the effectiveness has been due primarily to anti-microbial properties of honey. Healing processes will not usually occur unless infection is cleared from a lesion, and investigations involving swabbing wounds dressed with honey has shown that infecting bacteria are rapidly cleared.

In this respect honey appears superior to the expensive modern hydrocolloid wound dressings which are favoured in the art as a moist dressing. Although tissue re-growth in the healing process is enhanced by a moist environment, and deformity is reduced if the re-growth is not forced down by a dry scab forming on the surface, moist conditions also favour the growth of infecting bacteria. The difficulty facing the prior art is that antibiotics are ineffective in this situation while antiseptics cause tissue damage and thus slow the healing process. In contrast, honey causes no tissue damage and appears to actually promote the healing process.

While there is a need for moist dressings within the art, investigations involving honey as wound dressings have focussed primarily on unmodified honeys. As mentioned above, dressing wounds with honey has been the most prevalent form of investigation, essentially attempting to maintain raw honey in contact with a wound as part of a moist dressing. However, while such methods may be useful for investigative trials, the techniques can be relatively time consuming to apply and maintain, and may be impractical in a number of situations.

A primary cause of this is the relatively fluid nature of most honeys—i.e. honey is runny at body temperature. Due to this fluidity, especially at body temperature, localising honey to the desired area may be difficult. Difficulties may be less for an incapacitated person in a hospital bed, though these difficulties generally preclude its use as a simple wound dressing on an active person.

Containment of unmodified honey is thus a problem, and no simple practical solution has been proposed. The soaking of absorbent materials, such as gauzes, in a dressing to be applied over a wound and then held in place by a further covering is a possibility though tends to be messy and would be difficult to apply except in a clinical situation. Even then applying such a dressing can be relatively time consuming and require the use of an excessive number of relatively expensive sterilised coverings.

Another problem is that many wounds exude moisture and this causes the problem of further dilution of the honey exacerbating containment problems, especially where there is pressure on the dressing causing the diluted honey to be squeezed out. This dilution of the honey may also introduce other considerations such as a potential reduction in anti-bacterial activity due to dilution.

Accordingly, while the anti-bacterial properties of honey have been acknowledged, there are a number of practical problems to be overcome before honey can find widespread use as a practical dressing for wounds and other medical uses.

Similarly there are a number of problems associated with prior art 'moist' wound dressings, such as of the alginate type. The moist environment provided by these types of dressings favours the growth of microorganisms and accordingly they cannot be used on infected wounds, even though this may otherwise be the preferred choice of dressing. The use of many antibiotics have also failed to keep unwanted microbial growth in check when 'moist-type' dressings are used in certain situations of this type. Accordingly, medicine cannot always make use of the full potential of moist prior-art dressing types.

Reference will be made throughout the specification to the anti-microbial properties of honey. It is acknowledged that this is known in the art and a number of publications survey these properties. It is anticipated that a skilled addressee of the art would be familiar with the teachings of these publications insofar that many honeys possess antimicrobial properties, with some exhibiting more activity than others. Consequently, this document shall not seek to establish that certain honeys do possess anti-microbial properties, nor shall it seek to set out a specific list comparing the properties of all honeys which may or may not have been publicly documented. Again it will be relied upon that anti-microbial properties associated with honey have been established in the prior art By way of reference, some relevant documents which address this are given:

Molan, P. C. (1992) The antibacterial activity of honey. 1. The nature of the antibacterial activity. Bee World 73 (1): 5-28.

Molan, P. C. (1992) The antibacterial activity of honey. 2. Variation in the potency of the antibacterial activity. Bee World 73 (2): 59-76.

Willix, D. J.; Molan, P. C.; Harfoot, C. J. (1992) A comparison of the sensitivity of wound-infecting species of bacteria to the antibacterial activity of manuka honey and other honey. Journal of Applied Bacteriology 73: 388-394.

Cooper, R. A.; Molan, P. C. (1999) The use of honey as an antiseptic in managing Pseudomonas infection. Journal of Wound Care 8 (4): 161-164.

Cooper, R. A.; Molan, P. C.; Harding, K. G. (1999) Antibacterial activity of honey against strains of Staphylococcus aureus from infected wounds. Journal of the Royal Society of Medicine 92: 283-285.

A number of publications describe the large amount of variation in potency of antibacterial activity between different honeys. The variation can be as much as one-hundred-fold, and is due to varying levels of antibacterial factors in honey additional to the sugar content and acidity in which there is little variation.

A patent document of some interest is U.S. Pat. No. 5,177,065 by Silvetti. This document references the manufacture of wound dressings incorporating high levels of monosaccharides. In this document, it is the osmotic properties of concentrated sugar solution which are ascribed as providing any bactecriostatic effect. Consequently the described invention of Silvetti, and claims, concentrate on film-like compositions based on individual monosaccharides or mono-saccharide blends A very brief reference to honey is made in the prior art discussion of Silvetti, though only in terms of dismissing honey as a folk medicine which would appear to have no useful anti-bacterial effect in a wound healing preparation, such as the subject of that specification. Accordingly, while this document is of some interest, it teaches away from the use of honey in a wound covering form or composition, and instead teaches towards the use of predominantly monosaccharide solutions.

Accordingly, it is an object of the present invention to address the problems associated with the prior art, or at least to provide the public with a useful choice. It also appears from the prior art that the use of honey in a medicinal sense is useful though difficulties associated with its use prevent its full potential from being realised, and hence the present invention also seeks to address this.

Further aspects and advantages of the present invention will become apparent from the ensuing description which is given by way of example only.

DISCLOSURE OF INVENTION

According to one aspect of the present invention there is provided a medical composition comprising the combination of one or more honeys with a viscosity increasing agent.

According to another aspect of the present invention there is provided a medical composition, substantially as described above, in which at least 50% of the composition is honey.

According to another aspect of the present invention there is provided a medical composition, substantially as described above, in which the viscosity increasing agent is an alginate based material.

According to another aspect of the present invention there is provided a medical composition, substantially as described above, in which the viscosity increasing agent is a natural product based gelling agent.

According to another aspect of the present invention there is provided a medical composition, substantially as described above, in which the combination is such that the resulting composition is in the form of a firm, non-running gel.

According to another aspect of the present invention there is provided a medical composition, substantially as described above, in which the viscosity of the gel composition is such that it is suitable for application as an ointment or salve.

According to another aspect of the present invention there is provided a medical composition, substantially as described above, in which the viscosity of the gel composition is such that it is suitable for extrusion to fill wound cavities According to another aspect of the present invention there is provided a medical composition, substantially as described above, in which the gel-formed composition is substantially non-running at body heat.

According to another aspect of the present invention there is provided a medical composition, substantially as described above, in which the gel-formed composition is substantially non-running at 45° C.

According to another aspect of the present invention there is provided a medical composition, substantially as described above, in which the gel-formed composition includes moisture absorbing, trapping, or removing agents suitable for removing exudate from a wound such that the gel-formed composition remains substantially non-running for an extended period of time after application to a wound when compared to a similar composition in which the said water trapping, removing or absorbing agents are absent.

According to another aspect of the present invention there is provided a medical composition, substantially as described above, in which the combination of honey(s) and viscosity increasing agent(s) is such that the resulting combination is in the form of a formable and/or pliable putty that can be readily moulded into shape.

According to another aspect of the present invention there is provided a medical composition, substantially as described above, in which a putty-like composition is suitable for use as a wound dressing or covering.

According to another aspect of the present invention there is provided a medical composition, substantially as described above, in which a putty-like composition will substantially retain its state until pressure or force is applied to it.

According to another aspect of the present invention there is provided a medical composition, substantially as described above, in which a putty-like composition is substantially non-running—at up to 45° C.

According to another aspect of the present invention there is provided a medical composition, substantially as described above, in which a putty-like composition will slowly dissolve over time in bodily fluid.

According to another aspect of the present invention there is provided a medical composition, substantially as described above, in which a slowly dissolving putty-like composition is suitable for internal use.

According to another aspect of the present invention there is provided a medical composition, substantially as described above, in which the combination of honey(s) and viscosity increasing agent(s) is in the form of a flexible sheet.

According to another aspect of the present invention there is provided a medical composition, substantially as described above, in which a sheet-like embodiment is suitable for use as a wound dressing or covering.

According to another aspect of the present invention there is provided a medical composition, substantially as described above, in which a sheet-like composition possesses any one or more of the following characteristics:

the inclusion of water absorbing, trapping, or removing components to assist in the removal of free exudate;

is substantially non-running at body temperature;

will slowly dissolve in body fluids.

According to another aspect of the present invention there is provided a medical composition, substantially as described above, in which a composition of any of the foregoing forms will soften at body temperature, when compared to room or storage temperature, to allow it to conform to the configuration of the wound or surface to which it is applied or positioned, but which form remains substantially non-running—at up to standard body temperature, and more preferably to 45° C.

According to a further aspect of the present invention there is provided a wound dressing comprising at least a layer of a sheet or putty-like medical composition substantially as described above.

According to a further aspect of the present invention there is provided a wound dressing comprising a sheet composed of multiple layers of some or all of the compositions substantially as described above.

According to a further aspect of the present invention there is provided a wound dressing comprising a sheet composed of multiple layers of one, some or all of the compositions substantially as described above in addition to a fabric to provide additional cohesive strength.

According to yet a further aspect of the present invention there is provided a modified wound dressing comprising a medical composition substantially as described above, applied to cover at least an area on a backing portion. The backing portion may be an adhesive material that the area that extends beyond the medical composition serves to adhere the dressing to the surface of the skin surrounding a wound.

According to another aspect of the present invention there is provided a wound dressing, substantially as described in the preceding paragraph, in which the backing portion may comprise one or more layers of a suitable material.

According to another aspect of the present invention there is provided a wound dressing, substantially as described above, in which an area of an aforesaid composition overlies at least part of the backing portion.

According to another aspect of the present invention there is provided a wound dressing, substantially as described above, in which an area of the backing portion in which the medical composition is present, is defined by a number of smaller localised regions of the medical composition distributed within the larger area (in which the medical composition is present) on the backing portion.

According to yet a further aspect of the present invention there is provided a wound dressing or medical composition, substantially as described above, in which a honey present in same is chosen to have anti-microbial or bacteriostatic properties.

According to yet a further aspect of the present invention there is provided a wound dressing or medical composition, substantially as described above, in which a chosen honey includes a non-peroxide anti-microbial or bacteriostatic component.

According to yet a further aspect of the present invention there is provided a wound dressing or medical composition, substantially as described above, in which a selected honey has a water content of 17.1% or lower.

According to yet a further aspect of the present invention there is provided a wound dressing or medical composition, substantially as described above, in which a selected honey has $A_w$ of 0.94 or less, and preferably 0.86 or less.

According to yet a further aspect of the present invention there is provided a wound dressing or medical composition, substantially as described above, which has been sterilised with respect to clostridial spores by irradiation.

The present invention is directed to compositions, and products based thereon. Uses of the invention include applications in both human and veterinary medicine.

Preferred embodiments of the invention include one or more honeys exhibiting bacteriostatic or anti-microbial properties. It has been previously indicated that these properties in many honeys are well known, though there are difficulties associated with the use of honey for medical type uses. This includes the relatively fluid nature of honey and difficulties in localising it to the required area of treatment. There are also other associated difficulties, such as problems with wound exudate, and infection difficulties associated with moist dressings, which the present invention also seeks to address as part of its solutions for addressing the first problem.

Preferred embodiments of the present invention combine one or more honeys (for simplicity of description only one honey will generally be referred to in a composition described herein, though it should be remembered that this may be substituted by a blend of one or more honeys) in combination with a viscosity increasing agent. Typically the nature of this viscosity increasing agent is such that the fluidity of the resulting composition is increased to the point that the resulting composition is substantially non-running. By non-running is meant a composition which, if placed on an incline, will not flow down the incline. It is acceptable that the lower viscosity embodiments of the present invention may deform or bulge, but they should not break down and flow to any except the most minimal degree. For the purpose of defining the invention, such an inclination may be taken to be a slope of 45°.

Further, it is envisaged that some embodiments of the present invention may soften at more elevated temperatures. Accordingly, unless otherwise stated, non-running will generally be taken at a temperature of 20° C. In many instances also, it is desirable that the composition also remains non-running at body temperature—which will be taken to be 40° C. as many patients may also be exhibiting an elevated temperature. More preferably, compositions may be substantially non-running to 45° C. or higher.

The present invention may take a number of different forms. The less viscous forms will comprise a relatively soft gel which may be used as an ointment or salve. A potentially realisable advantage of the soft gels is that under the mild pressure of applying a covering, they may be forced into a wound to make intimate contact with the presented surface of the wound. While this represents one possible use of such embodiment it is also envisaged that there are other uses for such gel-like embodiments, such as for extruding into wound cavities. Previously mentioned have been applications such as gels and salves for use on ulcers and pustules. Varying gels may also be used intermediate the surface to which a dressing is to be applied, and the dressing. Preferably the dressing is a honey based dressing (such as the sheet type embodiments herein).

In some applications the gel may even be used to help retain or adhere the dressing in the desired location. For instance a honey based sheet embodiment typically possesses absorbent properties and can be employed to help increase the viscosity of a thin layer of gel with which it is in contact. Hence a small amount of a softer honey based gel can in some arrangements be used as an adhesive for a dressing—particularly for ulcers etc. It is also envisaged that there are other variations and embodiments of this principle, within the scope of the present invention.

Such embodiments may be stored and dispensed in different ways. They may be contained in tubes and dispensed in the manner of normal salves and ointments. They may also be contained in sealed capsules or packages which may be opened to allow the contents to be squeezed into the area of use. Other arrangements are also envisaged.

A further embodiment of the present invention is an embodiment which is perhaps best described as being putty-like. Such an embodiment may be moulded or plied into shape by finger pressure, and will substantially retain that shape even under soft-to mild pressure. This not only allows the thickness of the resulting composition, when used as a wound dressing, to be varied, but also allows it to be moulded for use in particular uses and locations. For instance, one could readily envisage its use when shaped to cover a wound on the bridge of a nose. This may be of some use in the area of cosmetic surgery.

As can also be appreciated, putty-like embodiments can also be used to provide some support and protection to some types of wounds, which gels and sheet-like embodiments (to be described later) may not be able to provide. Putty-like compositions of varying degrees of stiffness and pliability are envisaged within the scope of the present invention.

The third main category of embodiments according to the present invention are the sheet-like embodiments which comprise a formed sheet which can be laid over a wound. These may be pre-formed into a variety of shapes and sizes, though it is also envisaged that they may be easily trimmed to shape.

Typically such embodiments will be flexible enabling them to accommodate different contours and major irregularities on the surface over which they are applied. The degree of flexibility and softness may also be varied and it is also envisaged that the physical characteristics may slowly change over time when used in a moist dressing—especially as wound exudate, body warmth, and other parameters have effect on their composition.

The three main categories of physical forms in which medical compositions according to the present invention may generally fall into have been described above. Compositions from these general categories may also be used in the preparation of other products—for instance, such as a layer on a backing material in a wound dressing. This is not to say the present invention cannot take other forms than described above, though for case of description it is determined that the categorising of various embodiments into these three main groups is more convenient. This will assist in describing the various possible methods for their preparation and uses, which will be described later herein, and which preparations and uses may overlap between the various categories. There are no distinct boundaries between the categories, just bands in which one merges into the next.

It is also envisaged that apart from being non-running various embodiments of the present invention may possess other qualities. For instance, in some cases it is desirable for a medical composition according to the present invention to contact a wound or other surface as intimately as possible. Because there is often some surface irregularity, sheet and putty-like embodiments of the present invention may not necessarily make such intimate contact, whereas the gel-like embodiments will generally be more suitable for this purpose. This either allows the options of ensuring there is layer of a gel composition intermediate in an overlying layer of a sheet or putty-like embodiments, or alternatively looking at other methods of increasing the intimacy of contact.

One such latter method is to tailor the compositions such that while they may be relatively firm yet pliable at room temperature for handling and trimming, they substantially soften at body temperature, or at a temperature not too far above body temperature. This softening should be sufficient to allow the overlying composition to slowly mould into or contour to the wound—a process which may occur over minutes through hours. It is also envisaged, that in such embodiments a relatively thin layer of the material may be placed over the wound, and some gentle localised heat applied to soften the material and better conform with the surface to which it is applied. Ideally, for such elevated-temperature-softening embodiments, the temperature to which it needs to be heated should be in the range of 40°-50° C., and preferably towards the lower end of this range.

As a further or alternative method of increasing contact intimacy, embodiments which soften or swell in the presence of moisture can also be considered. In such cases, these may react to wound exudate, or even to a fine spray of water applied to the wound prior to the application of the dressing or covering. As many embodiments of the present invention are based on gelling substances, the selection of appropriate gels, or the incorporation of the appropriate amounts of various gels, makes this feasible. It is also envisaged that for this embodiment, as well as other embodiments, sheets comprising multiple layers of different formulations of compositions according to the present invention can be used. Hence a layer of water softening/swelling composition may be applied to a layer of a firmer composition. Analogous multi-layer technology may also be incorporated for the heat sensitive embodiments described above.

Other modifications which may be incorporated in various embodiments include means for reducing free moisture such as wound exudate. Such embodiments perform a partial mopping up action to ensure that the area under a dressing remains moist but not wet. Again this may involve the use of suitably selected gelling agents which can absorb a certain amount of moisture from the wound. Other components may also be added which perform such activities. These may include water absorbing components, and water removing components (which may work by chemical reaction) etc.

Embodiments of the present invention will, in their simplest form, comprise a combination of honey with a suitable viscosity increasing agent. Typically this agent will comprise a substance which forms a gel.

Selection of a suitable agent will involve a number of considerations. Such considerations include the suitability for the medical or the intended use; stability over time; compatibility with honey; and the ability to form a product having the desired physical properties—e.g. flexibility and strength etc. A number of other considerations may also be involved, and commonly these will at least be partially dictated by the requirements of the user and the intended purpose of a particular embodiment.

There are a number of suitable viscosity increasing agents available and, as previously indicated, preferred embodiments of the present invention will rely on gelling agents. A number of gelling agents are available including various gums and polysaccharides, alginates, and both synthetic and natural polymeric compounds. Such gelling agents are well known in the art,—in particular in the food and medical arenas—and will not be discussed in any specific detail herein apart from some representative examples given later herein. Some useful prior art referencing the use of gelling agents in medical type applications include U.S. Pat. No. 4,948,575, U.S. 5,674,524, U.S. 5,197,945, U.S. 5,735,812. U.S. 5,238,685, U.S. 5,470,576, U.S. 5,738,860, U.S. 5,336,501 and U.S. 5,482,932. There are undoubtedly a number of other patent specifications also referencing the use of various gels and polymers for medical use and in particular for wound dressings. Reference is made to these documents as a background to various viscosity increasing agents which may find use with the present invention.

Preferred embodiments rely upon the alginate salts to form a product of the desired viscosity (e.g. gel, putty or pliable sheet etc.). The alginates appear to be especially suitable for use with the present invention as the physical properties of the gel product appear to be relatively easily controlled. In addition, they have proven to be suitable for many medical type uses.

Typically the gelled alginates are combined with the honey and any other optional components. By alginate selection one can use an alginate which gels upon blending with honey, and/or rely upon another observed property of some alginates which is to gel when a polyvalent cation is introduced. For this latter type the gel promoting agents—typically polyvalent cations—can be introduced to form a gel product of the desired consistency. Any moulding, extruding, or forming processes should also be performed at this time so that the firmer embodiments 'set' into the desired configuration. Machining (e.g. slicing) into the final form—such as sheets cut from a block—can also be incorporated into any manufacturing process.

Alginates also have another potentially realisable, advantage in that introduced cations, or cations already part of the selected alginate, can be of benefit in some situations. For instance, calcium containing alginates may be selected for embodiments used where there is bleeding, as calcium can promote blood clotting. There are also a wide range of cations which can be present or introduced into the various alginates which can provide the user with some choice, though consideration would need to be given to any potentially cytotoxic ions, such as ammonium ions.

Other potentially useful gelling agents include the hydrocolloids and hydrogels. These components tend to absorb moisture to form a moist healing environment, though tend to absorb less fluid than the alginates. Consequently, it is envisaged that they would not be used for embodiments for heavily exuding wounds in which the alginates would tend to offer better performance. However, it is envisaged that combinations of various viscosity increasing agents may be used in particular embodiments, particularly if each imparts a slightly different property which helps fulfil a particular specification required by the user. For instance the hydrocolloids or hydrogels may be incorporated into gelling blends to vary properties such as the amount of fluid absorbed from a wound, etc.

Other optional materials may be included into various embodiments of the present invention. Some of these have been addressed previously, though there are also others. These may include various active pharmaceuticals, particularly to address concerns which extend beyond the ability of honey to address, or which augments or supplements the performance of honey. Some examples include fungicides, additional anti-bacterial agents etc.

Other optionally included components include filling materials which can change, the consistency and physical properties of an embodiment of the present invention. In particular, it is envisaged that the putties may include various solid particles to alter their physical properties. Even the physical properties of more solid embodiments, such as sheets, may also be altered by the inclusion of particular fillers. These fillers may include various particulate or granular materials which may be substantially inert or show some activity. Some examples include calcium carbonate, zinc oxide, barium sulphate etc. Other fillers may include flexible or soft components, such as small beads. These may be of polymeric materials. Various filling agents widely used in the pharmaceutical industry may be considered for use with the present invention.

Further, non-particulate materials, such as fibres, may also be included to alter the physical properties. The inclusion of randomly placed strands of alginate fibres, or even woven alginate fibre material, may be embedded or included in various embodiments. These, either in addition to or without other fillers, can also significantly alter the physical characteristics of various forms of the present invention.

As an extension of this principle, it is desirable for some embodiments of the present invention to be attached to a suitable backing material. This backing material may perform a number of roles, including acting as an intermediate between the honey composition and further backing layers, as a protective covering over the honey composition, or to further alter the physical properties of the honey composition. In particular it is envisaged that these arrangements will typically be used for the sheet-like embodiments of the present invention and may include a number of various manufacturing techniques including applying the un-gelled composition to the backing material so that it bonds to same during gelling, or techniques for bonding the gelled honey composition to the backing material after the honey composition has substantially gelled or been formed. Variations and other manufacturing techniques are also possible.

As a further consideration in manufacturing, at least part of the anti-bacterial effect in some honeys is due to the presence of an enzyme producing hydrogen peroxide. As for many enzymes this is temperature sensitive, and thus any manufacturing technique should avoid heating the honey to the extent that there is significant deactivation of the enzyme. In preliminary trials performed by the applicant, a maximum temperature of 60° C. was sustainable for up to one hour without any substantial enzyme degradation. These factors will influence any manufacturing technique.

BRIEF DESCRIPTION OF DRAWINGS

Further aspects of the present invention will become apparent from the following description which is given by way of example only and with reference to the accompanying drawings in which:

FIG. 1 are perspective diagrammatic views of some possible embodiments of a dressing;

FIG. 2 is a side view of a possible embodiment of a dressing, and

FIG. 3 are side views of further possible embodiments of a dressing.

BEST MODES FOR CARRYING OUT THE INVENTION

EXAMPLE 1

This group of examples is based on the use of alginates as a gelling and viscosity increasing agent for honey.

As a general procedure, finely powdered sodium alginate (the use of other alkaline metal alginates may also be considered) is blended with honey warmed to approximately 60° C. It is desirable that this temperature is not exceeded so as to avoid degradation of any hydrogen peroxide producing enzyme in the honey.

As the alginate slowly dissolves and absorbs water from the honey, a gel begins to form. Stirring should continue during this process so that as any yet unblended and ungelled alginate does nor settle out.

At this point a number of optional procedures may be followed depending upon the nature of the final product. For instance:

EXAMPLE 1a

For high viscosity products (e.g. sheets) the gel should be rolled into a sheet of the desired thickness as soon as it has gelled sufficiently to be able to handle the rolling procedure. The sheets should be maintained at a temperature high enough for hydration of the alginate to be completed and the full viscosity to be achieved for this particular product. By way of example this may be 60° C. for approximately one hour, or for longer periods at lower temperatures. This may vary according to the nature of the selected honey, the properties of the alginate selected etc., and thus some minor trial experimentation may be required to achieve an embodiment having the precise characteristics required by the user.

EXAMPLE 1b

As an alternative to Example 1a, a low viscosity product (e.g. a gel formulation or some putties) the blended mixture should be held at the elevated temperature to allow hydration of the alginate to be completed and the full viscosity achieved before it is packed or formed into the desired configuration. Some softer sheet-like embodiments may be also formed according to this method.

EXAMPLE 1c

For intermediate products, such as the putties, optional fillers and additives altering the physical properties of the resulting product (e.g. fibres) are preferentially introduced after the alginate has been substantially homogeneously dispersed throughout the honey and while the gelling process is occurring. The inclusion of such additives may also occur at other times, though it is noted that their inclusion prior to alginate addition may interfere with the ready blending of the alginate with the honey in some instances, while addition at a later stage may be more difficult for some embodiments e.g. the addition of fibres after gelling has substantially occurred.

EXAMPLE 2

Many alginates also exhibit gelling and cross linking properties promoted by the presence of polyvalent cations. These often tend to form tougher and less soluble alginate materials and thus may find use in a number of embodiments for altering physical characteristics of the resulting product. Typically it is envisaged that such modification will be used primarily for the sheet-like embodiments, particularly as a way of increasing the strength or solubility properties of the resulting sheet.

The polyvalent cations may be introduced in a number of ways, including the introduction of a soluble solution of polyvalent cations during the blending procedure. Preferably, this should be after gelling of the blend has initiated so as to avoid thickening reactions which interfere with the dispersion and hydrating of all of the sodium (or other) alginate being blended with the honey. However, as can be appreciated, adding polyvalent cations at different points can theoretically substantially alter the characteristics of the resulting product and thus a number of options remain open to the user to allow them to tailor the physical characteristics of various embodiments according to the intended end use and user requirements.

A range of polyvalent cations may be used, though toxicity considerations need to be given. It is anticipated that soluble calcium salts, such as calcium chloride, may be introduced at relatively low concentrations to promote the various gelling and cross linking reactions.

EXAMPLE 3

This example is directed to the forming of a gel into sheets. This may be achieved by placing a gel such as from Examples 1a or 1b between sheets of a non-wettable material—on a lab scale this comprised plastic or wax paper—and rolling it to a uniform thickness.

As a variation, a gauze fabric or other suitable material may be placed on top of the lower non-wettable sheet prior to the pouring of the gel. The rolling procedure is completed with the result being a sheet-like gel bonded to the gauze. FIG. 3a illustrates the result of such an embodiment, with the sheet of gelled honey (31) at least partially impregnating and bonding to the gauze or comparable material (33).

As a further variation, reinforcement may be provided in the centre of the gel. Here a layer of gel may be poured to cover the lower sheet, followed by placement of the gauze (or other reinforcing/backing material) followed by another layer of gel. The rolling procedure is then performed resulting in a sheet in which the gauze or fabric is embedded within the sheet. FIG. 2a illustrates the result of such a method with the gauze (or other suitable material) (23) embedded within the gelled honey (21). As a further option this may be bonded to a further backing sheet (25). This can be achieved by pouring the lower first layer of gelled honey (21) onto this layer (25), prior to placing the gauze (23) and top gel layer.

As a variation of this technique, the gel may be formed into two thin sheets, with the gauze then sandwiched between the sheets of the gel (still at an elevated temperature) and the rolling process re-performed on the sandwiched layers.

EXAMPLE 4

For a high viscosity product which is highly absorptive and suitable for use on heavily exuding wounds, the procedures described above are performed with 1 gram of sodium alginate with 5±2.5 grams of honey.

EXAMPLE 5

For a flexible product which is moderately adhesive and moderately absorptive and suitable for use on lightly exuding wounds, 1 gram of sodium alginate is combined with 10±2.5 grams of honey.

EXAMPLE 6

For a highly flexible and adhesive product suitable for use on dry wounds, 1 gram of sodium alginate is combined with 15±2.5 grams of honey.

EXAMPLE 7

For a lower viscosity product suitable for use as a gel (such as packed into a tube) to fill cavities and wounds, 1 grain of sodium alginate is combined with 17.5 grams or greater of honey, with the preferred amount being around 20 grams.

EXAMPLE 8

For a putty-like product, to the combinations outlined in Examples 6 and 7 is included sufficient fine filler material to achieve the desired consistency. Preferred filling agents include finely powdered calcium carbonate. Despite the insolubility of this component, it may nevertheless have some effect on any gelling reaction should it be added while gelling is still occurring. Previous, comments on polyvalent cations are referred to. The role of calcium in promoting blood clotting is also noted.

Other gelling agents, such as hydrogels, and various colloids, may be also included in these embodiments to vary the elasticity, pliability, and other physical characteristics of the putty. These may be in the form of blended components contributing to gelling, or even as firm components blended into the gel mixture as fillers.

These techniques may even be used in other embodiments For instance, FIG. 3b illustrates the presence of fibrous strands (35) (e.g. alginate fibres) and particulate matter (37) dispersed in the gelled matrix (31).

EXAMPLE 9

This example deals with the selection of honey for use with the present invention.

A large amount of this information is already referenced in the prior art identified earlier within this specification, and in particular publications by the inventor—Peter Molan. These publications reference the bacteriostatic and bactericidal effects of various honeys and thus reference may be made to this literature for identifying useful bactericidal honeys.

In addition, it is noted that while the osmolarity effect and peroxide effects of many honeys contribute to their antibacterial properties, research has also indicated that other components in some honeys also contribute to any bactericidal effects. It is considered, that for use in the present invention, these latter groups of honeys may be preferred, particularly for dressing and embodiments which may be stored for an extended period of time, or used under conditions which may result in degradation of any peroxide forming enzyme in the honey.

As can be envisaged also, the limitation on the maximum temperature to which the honey is subjected during manufacturing (to avoid enzyme degradation) may be overly restrictive for some embodiments. In such cases, honeys possessing bactericidal effects other than from the peroxide, may find use hare as it appears that some of the active components would be less sensitive to temperature.

Some preferred honeys for use with the present invention include honeys derived from leptospermum species such as, for instance, manuka and jellybush. These honeys tend to exhibit significant antibacterial properties arising from non-peroxide factors present, in addition to peroxide associated antimicrobial properties.

Additional honeys of interest include those derived from rewarewa (Knightia excelsa), kanuka (Kunzea cricoides), and from the honeydew present on bach (Nothofagus solandri).

EXAMPLE 10

An alternative method for the manufacturing process, that involves less heating of the honey than would be required to gel honey containing a powdered form of the gelling agent dispersed in it, is to hydrate the gelling agent in hot water then mix this solution of the gelling agent with the honey and then dry the mixture by applying heat and/or a flow of air to a film of the mixture. This alternative method for the manufacturing process is particularly useful for use with gelling agents which do not hydrate as readily as alginates, such as pectin or plant gums.

EXAMPLE 11

A final consideration in any manufacturing process is the presence of contaminants in honey. Being a natural product, there may be a variety of naturally occurring contaminants in the honey. This may include toxic substances from honeys sourced from particular flowers—ideally these honeys should be avoided unless there are some benefits for including such substances in a particular application. For instance, many toxic plants produce chemicals, such as digitalis, which have specific medical uses when used in controlled amounts.

A more prevalent problem is the presence of microbial spores such as clostridial spores. However, it has been demonstrated that these may be eliminated by gamma-radiation of honey, without destruction of any of the antibacterial activity of honey, and thus irradiation techniques may be considered for various embodiments

EXAMPLE 12

On a large scale, the application of gelled honey to a backing substrate may differ substantially from that described herein. It is envisaged that one option is to 'print' or 'paint' the gelling composition on to the substrate prior to it fully setting. Hence areas can be printed or painted on to the appropriate areas of a substrate material, which can then be trimmed into an appropriate Size, such as for a dressing.

FIG. 1a illustrates a dressing (11) which may have been produced by this method (but also by other techniques). Here an area (13) of gelled honey matrix has been applied centrally within a substrate (15).

FIG. 1b is an enlargement showing that in these embodiments the layer of gelled composition need not be continuous but may be made up of smaller regions (17). This may also allow a more open and breathable wound contact portion, which may be advantageous in some instance.

As can be appreciated also, various techniques described herein can be combined to produce more complex embodiments encompassing a number of different features

EXAMPLE 13

Uses of varying embodiments of the present invention are varied. It is envisaged that sheet like embodiments will be used in applications similar to those for which convention dressings are used.

Gels and salves can be used in the manner of conventional gels and salves. They may be applied directly into a wound cavity which represents an application for which many gels and salves possessing antibacterial properties may not be able to be used. Topical use inside the oral cavity for ulcers and abscesses of the mouth and gum diseases are another potential use of varying gel-like and other embodiments Gel-like embodiments may also be used as an intermediate between the substrate (e.g. skin or wound etc.) and a dressing, preferably a honey-based dressing such as described herein. This can help eliminate any air spaces, and fill irregularities in the substrate surface that the dressing is unable to conform to.

Further, if it is in a drying environment, many gel like embodiments may increase in viscosity. A gel used between dry skin (such as may surround a wound) and an absorbent dressing (such as a honey based sheet dressing described herein) can thicken over time as moisture migrates from it. In such a case the applied gel can act in the role of a mild adhesive or bonding agent to help keep the dressing in place. This can be of use in a number of applications, including for instance around ulcers, boils, pustules, carbuncles, acne and a variety of other 'dry' afflictions as well as taking advantage of normal dry skin surrounding wounds and other injured areas.

Thicker, pliable and mouldable embodiments have a range of potential applications including applications where Some support may be required in the wound area. Such embodiments may also find use in dental and oral applications, including temporary fillings or covers for teeth and gums.

As can be appreciated, there is a wide potential range of applications for the varying embodiments of the present invention. It will be appreciated that many such uses will become apparent to the skilled reader and addressee of the art in light of the description given herein, and it should be recognised that the limited range of possible uses and examples given herein are by way of example only and do not represent the entire range of potential uses.

EXAMPLE 14

The following data represents anecdotal trial results from use of varying embodiments of the present invention.

EXAMPLE 14a

In a leg ulcer where exudation was severe, initial treatment consisted of alginate based dressing sold for heavily exudating wounds. After no observable progress was made over extended period of time, a wound dressing according to the present invention was trialled. This consisted of 5 mm thick high alginic proportion (1 part alginate:5, part honey) pliable sheet positioned over wound and bandaged over. Wound dressing was changed daily and new sheet applied. Exudate was absorbed satisfactorily by dressing. An observable result was significantly reduced exudation from wound within a few days. Wound became manageable, and problems associated with prior art alginate dressings were eliminated.

EXAMPLE 14b

In a diabetic foot ulcer on foot underside, pliable sheet embodiment was used. Most prior art dressings were unsuitable for this location as squeezed out from weight on fool. This was not a heavily exudating wound though high alginic proportion (1:5) was used to provide firm sheet. Wound showed satisfactory healing despite known difficulty of healing of diabetic foot ulcers, and failure of prior art products tried up until use of present invention, to result in any improvement or healing.

EXAMPLE 14c

In a smashed jaw with eroding jaw bone from infection, there was no improvement over 18 month period using traditional techniques. Pain in patient was present and occasionally acute. In this case a pliable putty was used (1:5 ratio putty) and was fashioned to appropriate shape to cover wound. This dressing was replaced regularly at intervals of several hours (due to partial dissolving of putty by saliva). Wound healing progressed satisfactorily with rapid pain relief as added benefit.

EXAMPLE 14d

An alternative embodiment using agar, which sets into a solid gel, may he used on skin grafts to immobilise the graft—this is in accordance with current practice of occasionally using a dressing to hold graft in place by surgeons. Typically a sheet type embodiment utilising 1-10% agar by weight. Sheet of gauze is embedded into 1 mm thickness of gel (around 1% agar). Preparation may be by heating dissolved agar solution first and then stirring heated agar solution into cold honey. This is then applied over gauze to embed. The result is soft pliable sheet, with tackiness. This can be overlaid over graft or wound etc., and tackiness helps grip skin and prevent sliding.

This embodiment utilises a particulate gel (e.g. agar where particles stick to each other in a 3-d net) as opposed to a continuous gel (e.g. alginate) which tie up the water but where particles can roll over each other to give pliability and mouldable characteristics. Different embodiments may use one or other of these types of gelling agents. Can also blend different gel types to give products of intermediate characteristics.

EXAMPLE 14e

One other appln is to use softer formulation (1:10-1:20 alginate type typically) on acne. Similar uses on boils etc. Such embodiments are more discreet than sticking plaster and may also be used for mouth ulcers. Acne embodiments may be in the form of a gel, salve, or ointment, and may also include other components such as pigments (preferably flesh coloured) and/or sulphur.

Aspects of the present invention have been described by way of example only and it should be appreciated that modifications and additions may be made thereto without departing from the scope thereof.

What is claimed is:

1. A formable or pliable, or both, *flexible sheet or a pliable putty* composition for dressing wounds, comprising a combination of a medicinal amount of at least one honey and at least one gelling compound, wherein the amount of the gelling compound in the composition is sufficient to cause the composition to be a formable or pliable, or both, solid *flexible sheet or a pliable putty* that is mouldable to fit a wound to which the composition is applied, and wherein at least 50% by weight of the composition is said at least one honey.

2. The composition of claim 1, wherein the at least one gelling compound is an alginate-based material.

3. The composition of claim 1, wherein the at least one gelling compound is a natural-based gelling compound.

4. The composition of claim 1, further comprising a gelling compound in the form of a continuous gel.

5. The composition of claim 1, wherein the at least one gelling compound causes said composition to be in the form of a particulate gel.

6. The composition of claim 1, which is substantially non-running at a temperature at least as high as body temperature.

7. The composition of claim 6, which is substantially non-running at about 45° C.

8. The composition of claim 1, further comprising at least one moisture absorbing, trapping, or removing compound suitable for removing aqueous exudate from a wound, and wherein the amount and nature of said exudate removing compound is such that the composition remains substantially non-running for an extended period of time after application to a wound when compared to a similar composition in which the said water trapping, removing or absorbing compound is absent.

9. The composition of claim 1, which has the property of absorbing bodily fluid over a period of time not less than about the time required for the wound to heal.

10. The [compound] *composition* of claim 9, which is suitable for internal use.

11. The composition of claim 1, having a viscosity that is sufficient to render the composition extrudable to fill wound cavities.

12. The composition of claim 1, which is a medicinal composition in solid plastic form.

[13. The composition of claim 1, in the form of a flexible sheet.]

14. The composition of claim [13] *1*, comprising a combination of gelling compounds.

15. The composition of claim [13] *1*, comprising at least one gelling compound that is formable into a continuous gel, and at least one gelling compound that is formable into a particulate gel.

16. The composition of claim 1, further comprising at least one of a pigment or sulphur.

17. The composition of claim 16, which comprises a pigment and said pigment is flesh-colored.

18. The composition of claim 1, wherein said at least one honey has antimicrobial or bacteriostatic properties.

19. The composition of claim 18, wherein said at least one honey comprises a non-peroxide anti-microbial or bacteriostatic component.

20. The composition of claim 1, which is sterilized against clostridial spores by irradiation.

21. A wound dressing, comprising the composition of claim 1.

22. The wound dressing of claim 21, further comprising a reinforcing material.

23. The wound dressing of claim 22, wherein the reinforcing material is selected from the group consisting of gauze, mesh, random fibers and woven fabric.

24. The wound dressing of claim 22, wherein the reinforcing material is embedded in the composition.

25. A modified wound dressing, comprising the wound dressing of claim 22, applied to a backing sheet.

26. The modified wound dressing of claim 25, wherein backing sheet comprises at least one layer.

27. The modified wound dressing of claim 25, wherein the backing sheet comprises adhesive areas other than in areas coextensive with the wound, thereby allowing the modified wound dressing to be applied and adhere to unwounded skin or other application surface.

28. The modified wound dressing of claim 25, comprising a backing sheet on which is present a wound patch, and in which said composition is present.

29. The modified wound dressing of claim 28, wherein said wound patch comprises a plurality of localized regions comprising said composition distributed within a larger area of said backing sheet.

30. A method of treating acne, comprising applying the wound dressing of claim 25 thereto.

31. A method of treating a pustule, comprising applying the wound dressing of claim 25 thereto.

32. A method of treating burns, comprising applying the wound dressing of claim 25 thereto.

33. A method of treating recovering skin grafts comprising applying the wound dressing of claim 25 thereto.

34. A method of treating ulcers, comprising applying the wound dressing of claim 25 thereto.

35. A method of treating oral wounds, comprising applying the wound dressing of claim 25 thereto.

36. A method of treating wounds, comprising applying the wound dressing of claim 25 thereto.

37. The method of treating wounds of claim 36, wherein an exuding wound is treated.

38. A method of treating acne, comprising applying the wound dressing of claim 21 thereto.

39. A method of treating a pustule, comprising applying the wound dressing of claim 21 thereto.

40. A method of treating burns, comprising applying the wound dressing of claim 21 thereto.

41. A method of treating recovering skin grafts, comprising applying the wound dressing of claim 21 thereto.

42. A method of treating ulcers, comprising applying the wound dressing of claim 21 thereto.

43. A method of treating oral wounds, comprising applying the wound dressing of claim 21 thereto.

44. A method of treating wounds, comprising applying the wound dressing of claim 21 thereto.

45. The method of treating wounds of claim 44, wherein an exuding wound is treated.

46. A method of treating a pustule, comprising applying the composition of claim 1 thereto.

47. A method of dressing a wound, comprising applying the composition of claim 1 thereto.

48. A method of treating an ulcer, comprising applying the composition of claim 1 thereto.

49. A method of treating burns, comprising applying the composition of claim 1 thereto.

50. A method of covering skin grafts, comprising applying the composition of claim 1 thereto.

51. A method of treating acne, comprising applying the composition of claim 1 thereto.

52. A method of treating exuding wounds, comprising applying the composition of claim 1 thereto.

53. A method of treating oral wounds, comprising applying the composition of claim 1 thereto.

* * * * *